United States Patent [19]
Tai et al.

[11] Patent Number: 4,934,815
[45] Date of Patent: Jun. 19, 1990

[54] APERTURE SAMPLING COHERENCE SENSOR AND METHOD

[75] Inventors: Anthony M. Tai, Northville; John N. Cederquist, Ann Arbor, both of Mich.

[73] Assignee: Environmental Research Institute of Michigan, Ann Arbor, Mich.

[21] Appl. No.: 217,775

[22] Filed: Jul. 5, 1988

[51] Int. Cl.$^5$ ............................................... G01B 9/02
[52] U.S. Cl. ..................................................... 356/354
[58] Field of Search .................. 356/354, 358; 250/227

[56] References Cited

U.S. PATENT DOCUMENTS 4,350,443 9/1982 Williamson ......................... 356/358
4,743,752 5/1988 Olsen et al. .......................... 250/227

OTHER PUBLICATIONS

Creath et al., "Vibration-Observation Techniques for Digital Speckle-Pattern Interferometry", J. Opt. Soc. Am. A., vol. 2, No. 10, Oct. 1985.

Primary Examiner—Leon Scott, Jr.
Attorney, Agent, or Firm—Krass and Young

[57] ABSTRACT

In a speckle imaging process, the contribution of non-uniform, incoherent background illumination is removed via an aperture sampling technique. A pair of uncorrelated speckle images are produced and subtracted from one another to eliminate the non-coherent background contribution. The result of this subtraction is rectified so as to provide a signal which may be displayed on a video display. Disclosed are techniques for real time video display of enhanced speckle images as well as techniques for visualizing vibrational modes and surface roughness mapping.

17 Claims, 1 Drawing Sheet

APERTURE SAMPLING COHERENCE SENSOR AND METHOD

FIELD OF THE INVENTION

This invention relates to optical systems and methods in general and in particular to systems and methods for reducing the contribution of the noncoherent component in a speckle image.

BACKGROUND OF THE INVENTION

Speckle imaging and interferometric techniques are utilized to provide an indication of the state of the surface of an object and are finding ever growing applications in science and industry. Speckle techniques rely upon the interference of a field of coherent light as it is reflected from an irregular surface of an object so as to produce an image characterized by a fine pattern of speckles Speckle images thus generated may be further processed to provide information relating to both the surface topology such as roughness, contours and the like as well as the vibrational modes of the object.

In many speckle imaging and speckle interferometric applications, there is a need to separate the coherent speckle image from a nonuniform non-coherent background. The non-coherent field may be generated by a non-coherent illuminating source, or it may be due to the decorrelation of a coherent incident field by an intervening medium, or by the physical characteristics, such as roughness or vibration, of the reflecting surface. For example, in speckle imaging, a coherently illuminated target may be imaged through a scattering medium where the scattering reduces significantly the contrast of the speckle image. Removing the non-coherent component in the received image field will recover the full contrast of the speckle image. Similarly, surface vibration of an object will decorrelate an incident coherent field and the vibrational modes of the object may be made distinct by removing the portion of the image field decorrelated by the surface motion.

Speckles are formed when a coherently illuminated diffuse or rough object is imaged with a finite imaging aperture. Due to the finite size of the point spread function or impulse response (i.e., the degree to which a true point source is focused by the system) of the imaging system, the optical field at a point in the image field is composed of a large number of scattered contributions with random amplitude and phase. When the contributions are fully coherent and with the same linear polarization, the optical field is the coherent sum of the complex amplitudes contributed by the scatterers within the point spread function. The resulting image of the extended diffuse object exhibits a random salt and pepper like pattern called speckle. The intensity characteristics of fully developed coherent speckles are described by a negative exponential intensity probability distribution and unity contrast where contrast is defined as the standard deviation of the intensity fluctuation divided by the mean.

With an non-coherent object field on the other hand, the contributions of the scatterers within the point spread do not interfere and they add their intensities. The image will not be speckled and for an object surface with uniform reflectance, the speckle contrast will be zero. For the intermediate case where the field is partially decorrelated or partially coherent, the speckle contrast will fall somewhere between 0 and 1 depending on the degree of coherence.

Previously employed techniques for removing the non-coherent component in the image field detect the difference in coherence by interfering the image field with a coherent reference beam. Typically, the resulting image field is detected, digitized and stored in a frame grabber on other memory device. Then the phase of the reference beam is shifted by $\pi$. The phase shift produces no effect on the incoherent portion of the image field but it inverts the contrast of the coherent speckle image since constructive interference between the coherent image and the reference beam becomes destructive and visa versa. Subtracting the two frames removes the incoherent component which is unchanged between the two frames. What remains is a final image due only to the coherent portion of the detected image.

Such techniques are described in the following publications: K. Creath and G. A. Slettmoen "Vibration Observation Technique for Digital Speckle Pattern Interferometry" J.Opt. Soc. Am. A, 2, 1629-1636 (1985); K. Creath, "Digital Speckle Pattern Interferometry (DSPI) Using a 100×100 Imaging Array" Proc. Soc. Photo-Opt. Instrum. Eng., 501, 292 (1984); and O.J. Lokberg, J. T. Malmo and T. A. Slettmoen, "Interferometric Measurements of High Temperature Objects by Electronic Speckle Pattern Interferometry", Appl. Opt. 24, 3167-3172 (1985). Such heretofore available techniques for the reduction of non coherent image field function relatively well in laboratory situations. However, they are difficult to implement and utilize because of the need of employing several precisely aligned beams of coherent light as well as the need for phase shifting a reference beam between alternate image frames. Such a precisely disposed imaging system is very prone to vibrational interference from the instrument itself. Precise fringe monitoring is often necessary to ensure a high degree of mechanical stability. What is needed is a technique to remove the incoherent contribution in speckle imaging and interferometry which eliminates the need for a coherent reference beam thereby avoiding stability problems which have heretofore prevented widespread field use of such techniques.

The present invention provides method and apparatus for speckle imaging and speckle pattern interferometry which eliminates or substantially reduces the contributions of incoherent background illumination without the necessity for the use of a reference beam. It has been found that a pair of uncorrelated speckle images provided by the aperture sampling technique of the present invention may be appropriately processed so as to subtract background contributions. The present invention is particularly advantageous insofar as it provides a rugged system for speckle imaging, which can significantly reduce the incoherent background illumination and enhance the contrast of the speckle image or fringe pattern, which system is readily adapted for relatively high speed processing so as to allow for the production of real time imaging.

SUMMARY OF THE INVENTION

In accord with the principles disclosed herein there is provided apparatus for generating a speckle image of an object, which apparatus removes incoherent portions of the detected image field. The apparatus includes a source of coherent or partially coherent light adapted to illuminate the object so as to produce a light field reflected therefrom. The apparatus further includes sampling means adapted to (1) sample a first portion of the input light field and produce a first speckle image therefrom and (2) sample a second portion of the input light field disjoint from the first portion and produce a second speckle image therefrom, the speckle pattern in the second image being uncorrelated with the first image. The apparatus also includes processing means adapted to subtract the first speckle image from the second speckle image and rectify the results of the subtraction.

The sampling means may include an optical system having at least one lens and may further include a pair of apertures that can be individually shuttered. A first aperture can be disposed so as to sample the first portion of the input light field and a second aperture is separated from the first aperture by at least the diameter of a speckle and disposed so as to sample a second portion of the light field and produce the second speckle image.

In yet other embodiments, the sampling means may include a single aperture disposed so as to be moved between a first position wherein the aperture samples a first portion of the light field and a second position disjoint from the first position by at least the diameter of a speckle, wherein the aperture samples a second portion of the light field. In a variation of this embodiment, the aperture may be moved between the first and second positions at a frequency of at least 30 Hertz so as to provide at least 15 disjointed pairs of images per second. The pairs of images thus produced may be subtracted and rectified so as to provide a real time speckle image updated at video rates.

The processing means may be further adapted to digitize and store the first and second speckle images so as to allow for digital processing thereof and toward this end, the processing means may further include a computer such as an image processing computer.

It is generally preferred that the processor further include a video camera disposed so as to receive the speckle images and convert them into electronic signals. Cameras including charge coupled devices are particularly advantageous.

The apparatus may also be employed to visualize the vibrational modes for an object by a technique of time-averaged speckle interferometry where a moving portion of an object decorrelates a coherent beam and the dual aperture technique removes this decorrelated contribution. The apparatus may also be adapted to provide information regarding surface texture of an object having a plurality of surface features each having a given surface height, by providing the apparatus with a source of at least partially coherent light adapted to illuminate the object with light having a longitudinal coherence length of the same order as the surface heights of the features of interest.

There is also provided a method for the reduction of the non-uniform non-coherent background of a speckle image. The method includes the steps of illuminating the object with coherent light so a to provide a reflected field of coherent light therefrom, sampling a first portion of the reflected field so as to provide a first speckle image and sampling a second portion of the reflected field disjointed from the first portion by at least the diameter of a speckle so as to provide a second speckle image uncorrelated with the first. The method includes the further steps of subtracting the first and second speckle images and rectifying the result of the subtraction whereby the contribution of non-coherent light to the speckle image is removed. In some embodiments it is preferred that the first and second speckle images be digitized prior to the subtraction thereof. The steps of sampling the first and second portions of the reflected field may include the further step of providing an aperture disposed so as to sample the reflected field and provide a speckle image of the illuminated object, disposing the aperture at a first position so as to provide a first speckle image and moving the aperture to a second position disjointed from the first position by at least the diameter of a speckle whereby the aperture provides a second speckle image uncorrelated with the first speckle image. In yet other embodiments a single aperture may be moved between a first and second disjointed position so as to provide the uncorrelated images. The method may be readily adapted for providing information regarding surface texture of an object having features of given heights. In this instance the method will further include the step of illuminating the object with partially coherent light having a coherence length less than the heights of the surface features of interest.

DETAILED DESCRIPTION OF THE INVENTION

Figure 1:
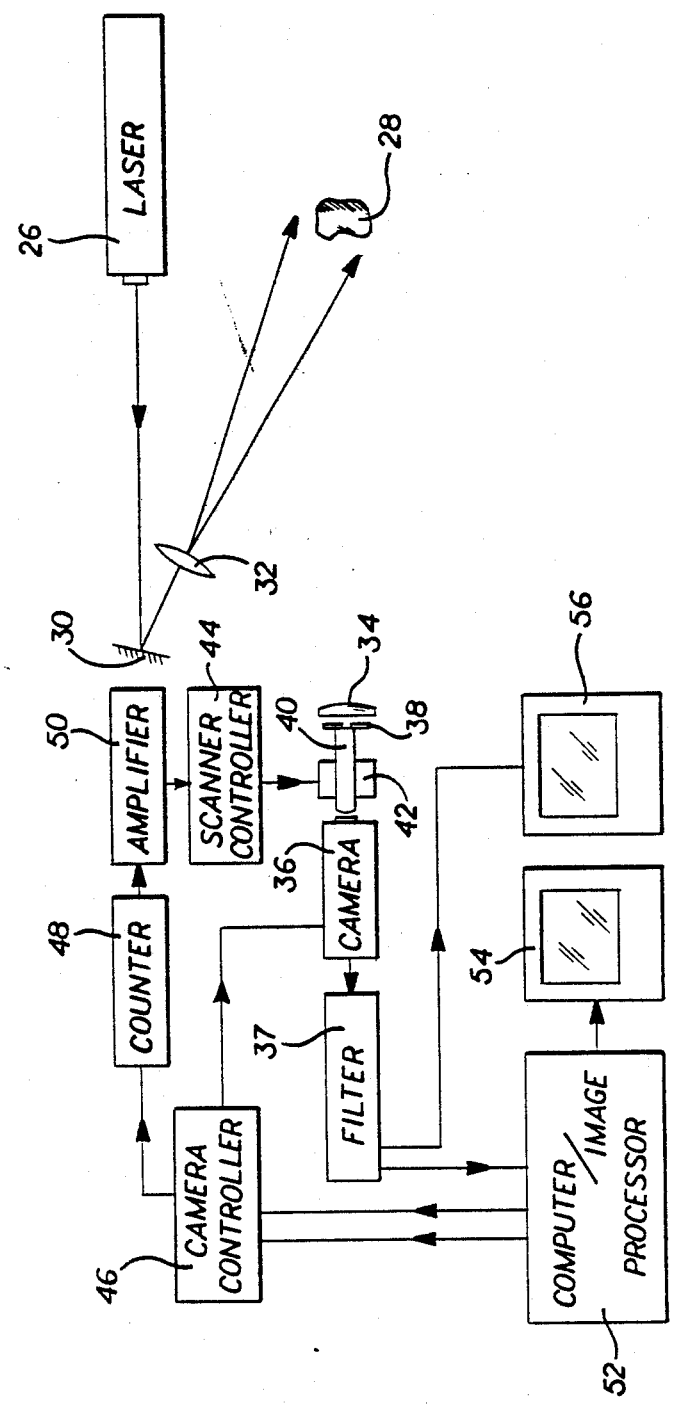
FIGURE 1 is a schematic depiction of one particular apparatus structured in accord with the principles of the present invention.

The present invention is directed to the elimination or significant reduction of the non-uniform, non-coherent image field present in a speckle image. If a pair of images include the same non-coherent image field it is clear that subtraction of those images from one another will cancel out the non-coherent contribution; however, it is not practical to undertake such subtraction because the operation will also cancel out the foreground information of interest thereby providing a result devoid of any useful information.

If however, it were possible to determine conditions for creating two speckle images of the same object scene which, upon subtraction of the intensity of one from the other will produce an image with a high degree of contrast, background reduction by such subtraction could be undertaken. It has been found in accord with the principles of the instant invention that the subtraction of two uncorrelated speckle patterns will provide an output signal with all the incoherent components removed from the image field, leaving a speckle image with unity contrast. By "uncorrelated speckle pattern", it is meant speckle patterns that have the same intensity statistics such as mean and standard deviation but have no statistical relationship between each other. The summation of the intensities of two uncorrelated speckle patterns will provide a signal with minimum speckle intensity variation while the subtraction of the intensity of two uncorrelated speckle patterns will provide a signal with maximum speckle intensity variations.

The fact that a new speckle pattern is obtained by subtracting a first speckle pattern from a second uncorrelated speckle pattern and rectifying the result is shown below for the class of fully developed speckles. In such instance the probability density distribution of the intensity of a speckle pattern is given by:

$$P_I(i) = \frac{1}{A} \exp(-i/A) \tag{1}$$

where A is the mean intensity of the speckle pattern. We can compute the probability density distribution of an image obtained by subtracting two uncorrelated speckle images with the same statistical properties and rectifying the result. That is, if $I_1$ and $I_2$ are random variables corresponding to the intensities of the two uncorrelated speckle patterns we are to determine the probability density distribution of I where $I=I_2 - I_1$, wherein the value of I like $I_1$ and $I_2$ will take on only positive values.

I is defined within a sample space S which can be decomposed into subsets or events; Since $I_1$ and $I_2$ are identically distributed, E' and E'' are equally likely to occur. Thus:

(2) $PI[E'] = PI[E''] = \frac{1}{2}$ $P_I[S] = P_I[E' \cap E''] = 1$

The probability density distribution of I can be written as:

(3) $P_I(i \epsilon S) = P_{I[E']} P_I(i \epsilon E') + P_I[E''] P_I(i \alpha E'')$ with $I_1$ and $I_2$ being identically distributed, $P_I(i \epsilon E') = P_I(i \epsilon E'')$ and equation (3) can be written as $p_I(i) = P_I(i \epsilon E')$ (3) (computing the probability that I is greater than or equal to i given that $I_2$ equals $i_2$ and $i \epsilon E'$, there is obtained, $$F_I(i/I_2 = i_2, i \epsilon E') = \frac{1}{A} \int_0^{i_2 - i} \exp[-i_1/A] di_1$$
$$= \{1 - \exp[-(i_2 - i)/A]\} \text{ for } i_2 \geq i$$
$$= 0 \text{ for } i_2 < i$$

The probability that I is greater than or equal to i is therefore equal to:

$$F_I(i/i \epsilon E') = \frac{1}{A} \int_i^\infty \exp[-(i_2 - i)/A] \cdot \exp[-i_2/A] di_2 + \frac{1}{A} \int_i^\infty \exp[-i_2/A] di_2 = \frac{1}{2} \exp[-i/A] \quad (6)$$

Since $$F_I(i/i \epsilon E') = P_I[E'] \int_i^\infty P_I(i) di' \quad (7)$$

we have $$p_I \times (i) = \frac{1}{A} \exp[-i/A] \quad (8)$$

which is identical to that of a speckle pattern. Therefore, subtracting two uncorrelated speckle patterns with the same statistics and rectifying the results restores the original speckle pattern.

It has been found that for an object plane which is sufficiently far from a lens or other sampling means utilized to provide speckle images, the light field at the collecting aperture corresponds to the complex spatial spectrum of the field scattered by the object. By using different portions of the input field, different bands of the spectrum are sampled. The light field at the aperture of the lens is uncorrelated over a spatial difference of lambda R/D (the size of a speckle) where lambda is the illumination wavelength, R is the distance of the object to the lens and D is the diameter of the illuminated area. Thus speckle images formed from different portions of the input light field which are disjointed and separated from one another by at least a speckle width are uncorrelated.

The principles of the present invention may be implemented in a variety of speckle imaging systems suited for various applications provided that the imaging system is adapted to produce a pair of uncorrelated speckle images and further includes means for subtracting those images. Production of uncorrelated images may be accomplished by the use of disjointed portions of the two separate optical systems disposed so as to sample a field of reflected light emanating from the object of interest. Alternatively, a single movable aperture may be utilized to repetitively sample disjointed portions of the reflected light field.

Referring now to FIG. 1, there is shown one particular embodiment of the present invention. FIG. 1 illustrates a block diagram for a real time aperture sampling digital speckle pattern interferometer adapted to provide a video image. The apparatus of FIG. 1 includes a source of coherent light such as a laser 26 disposed to illuminate an object 28 with a beam of coherent light so as to produce a speckle image therefrom. Toward this end the laser has associated therewith an optical system, illustrated herein as including a mirror 30 adapted to direct the beam emanating from the laser and a beam expander 32 disposed so as to provide a relatively wide field of illumination upon the object 28. Obviously, the present invention may be practiced with a wide variety of lasers and various optical systems as is well known to those of skill in the art. In the illustrated embodiment, the laser is a Argon ion laser operating at a wavelength of 0.5145 micrometers.

The apparatus further includes a lens 34 disposed so as to image the light reflected from the object 28 onto a video camera 36 so as to provide a speckle image. The lens has associated therewith an aperture 38 positioned so as to select a portion of the field of light incident upon the lens. As illustrated the aperture 38 is positioned between the lens and the camera. Obviously, other optical systems including a plurality of lenses as well as alternate positioning of the aperture may be similarly employed. The aperture 38 is mounted upon a pivot arm 40 connected to a scanner 42 and the scanner and pivot arm 40 cooperate to move the aperture 38 within the field of light focused by the lens.

As illustrated the aperture scanner 40 is operated by a scanner controller which is driven by the vertical sync pulses provided by the video camera controller 46. In the illustrated apparatus 60 Hertz vertical sync pulses from the video camera controller 46 were used as a clock input to a two count counter 48 thereby producing a synchronous 30 Hertz squarewave which is amplified by the amplifier 50. This amplifier signal is utilized to drive the scanner controller 44 causing it to operate the scanner 42. In this manner the aperture was moved across the imaging lens at a rate of 30 Hertz. Care was taken to assure that the aperture was moved sufficiently to sample disjointed portions of the input field and thereby provide uncorrelated speckle images to the video camera 36.

In this manner 15 pairs of uncorrelated images were produced every second. The image pairs were processed in the computer 52 as described previously, to remove incoherent background. Specifically, alternate frames were subtracted then rectified through the use of a look-up table. The resultant signal was converted to the appropriate video format and displayed on a video monitor 54.

In order to produce a real time video display, the imaging processing computer 52 includes a pair of video buffers therein. While the image content of the first video frame buffer is being displayed upon the monitor 54 the next two image frames are acquired and processed as previously described and stored in the second video frame buffer. After 1/15 of a second the display pointer is switched to the second video frame buffer to display the new processed image on the monitor 54 and the first video frame buffer is now free to process the next pair of frames. Obviously, the system can be modified to achieve still higher rates by increasing the rate at which the aperture 38 is moved and by appropriately readjusting the timing of the processor. As illustrated, the apparatus may further include a filter 37, to remove unwanted noise from the camera signal and an additional monitor 56 adapted to display the "live" unprocessed image.

An apparatus similar to that of FIG. 1 was employed to test the effectiveness of the present invention in enhancing a speckle image embedded in an incoherent background bias. A diffuse three-dimensional target was illuminated with laser light. The light level was adjusted such that the illuminated object 28 was just bright enough to be seen by the video camera 36. A strong non-uniform incoherent background was added by illuminating the detector array of the camera with an incandescent light, the brightness of which was adjusted such that the brightest part nearly saturated the detector. The resultant image produced thereby exhibited virtually no detail on the live image display 56. However the processed image displayed on the terminal 54 exhibited very high contrast and the hidden object was displayed.

A real time video system such as that of FIG. 1 may be advantageously applied to many dynamic situations. For example, the system may be employed to detect vibrational modes of an object. Moving surfaces decorrelate a scattered light field therefore a very low contrast speckle image is produced by rapidly moving portions of a vibrating object. Stationary areas of the object correspond to vibrational nodes and form high contrast speckles thereby allowing visualization of the vibrational pattern. By the use of the present invention the incoherent light from the rapidly moving portions is effectively eliminated and the contrast of the speckle image at the nodal points is increased thereby clearly visualizing nodal patterns in vibrating objects.

The principles of the instant invention may be further applied to generate information regarding the surface texture of objects. It is well known that speckle contrast is directly related to the roughness (surface height variation) of the scattering surface for an object under coherent illumination, where the longitudinal coherence length of the illumination is close to the magnitude of the surface height variations. When the surface height variation of the features on an object is larger than the coherence length of the illuminating source, the field forming the image becomes partially decorrelated. The degree of coherence, as measured by the speckle contrast, is therefore a function of the magnitude of the surface height variation, and indicative of texture. The intensity of an image produced by the aperture sampling technique of the present invention is directly proportional to the speckle contrast. Thus, for an object scene with uniform reflectance the intensity distribution of the processed image is a direct representation of the surface roughness distribution of the object.

An apparatus similar to that of FIG. 1 was utilized to generate a surface roughness map of a test object comprised of a smooth white paper cardboard silhouette affixed to a white piece of foam. The surface of the foam had many tiny pores while the surface of the cardboard was quite smooth. A dye laser with no internal cavity or dispersive element was used as the illuminating source. The spectral band width of the beam was two nanometers, which provided a longitudinal coherence length of approximately 150 microns. Under incoherent illumination the test object exhibited very low contrast. Illumination with the dye laser produced a high contrast speckle image of the smooth cardboard cutout, but the image was embedded in an incoherent background and therefore exhibited relatively low signal to noise ratio. By applying the techniques of the present invention the decorrelated, non-coherent background contribution was minimized and the contrast of the speckle image was enhanced. In this manner the part of the object field with smooth surfaces appeared relatively bright and speckled while the areas with rough surfaces appeared quite dark.

This technique may be utilized to generate a surface roughness map. For example the processed image can be normalized with regard to the incoherent image so as to remove the effect of differing surface reflectances. The resultant image brightness is then directly proportional to the speckle contrast which in turn is determined by the magnitude of the surface height variations.

It should be noted that the dual beam approach to speckle imaging known in the prior art cannot be used for generating surface roughness images or in any other situation where the depth of the object being imaged is longer than the coherence length of the laser source. Thus it will be appreciated that the aperture sampling technique of the present invention not only provides a system having a high degree of tolerance to mechanical variations but also extends the techniques of speckle interferometry to heretofore inaccessible areas.

It should thus be appreciated that the present invention provides method and apparatus for reducing background bias in speckle images as well as for generating and processing speckle images of objects having 3-dimensional features greater than the coherence length of the light source employed. The invention is also capable of providing techniques and apparatus for the generation of surface roughness maps. Obviously, many variations of the systems and methods disclosed herein may be practiced in accord with the principles of the present invention. The foregoing drawings, discussion and description are merely meant to be illustrative of the principles of the present invention and not to be limitations upon the practice thereof. It is the following claims, including all equivalents, which define the scope of the invention.

We claim:

1. Apparatus for providing a speckle image of an object having reduced contributions from non-uniform, incoherent illumination, said apparatus including:
   a source of at least partially coherent light disposed to illuminate an object so as to produce a light field reflected therefrom;
   sampling means operative to (1) sample a first portion of the reflected light field so as to provide a first speckle image therefrom and (2) sample a second portion of the reflected light field spatially separated from the first portion by a distance sufficient to provide a second speckle image therefrom which is uncorrelated with said first image; and processing means operative to (1) subtract said first speckle image from said second speckle image so as to provide an output signal and (2) rectify the output signal.

2. An apparatus as in claim 1, wherein said sampling means includes at least one lens.

3. An apparatus as in claim 1, wherein said sampling means includes a pair of apertures, a first aperture disposed to sample a first portion of the light field so as to provide the first speckle image and a second aperture separated from the first aperture by at least the diameter of a speckle and disposed to sample a second portion of the light field and provide the second speckle image.

4. An apparatus as in claim 1, wherein said sampling means includes a single aperture operatively disposed to be moved between a first position wherein said aperture samples a first portion of the light field and a second position spatially separated from the first position by at least the diameter of a speckle wherein said aperture samples a second portion of the light field.

5. An apparatus as in claim 4, further including means for moving said aperture between said first and said second positions at a frequency of at least 30 Hertz.

6. An apparatus as claim 5, wherein said processing means is operative to subtract alternate speckle images produced at said first and second positions, and rectify said output signal, so as to produce new speckle images having a reduced contribution from non-uniform incoherent illumination, at a rate of at least 15 Hertz.

7. Apparatus as in claim 6, wherein said processing means further includes a video display and said apparatus is operative to provide a real-time video display of said new speckle images.

8. An apparatus as in claim 1, wherein said processing means is further operative to digitize said first and second speckle images.

9. An apparatus as in claim 1, wherein said processing means comprises a computer.

10. An apparatus as in claim 1, further adapted to provide information regarding a surface texture of an object having a plurality of surface features each having a given surface height, wherein said source of at least partially coherent light is operative to illuminate an object with coherent light having a coherence length similar to the magnitude of the given surface height of the features.

11. An apparatus as in claim 1, wherein said processing means further includes a video camera disposed so as to receive said speckle images and convert them into electronic signals.

12. An apparatus as in claim 11, wherein said camera includes a charge coupled device.

13. A method for the reduction of the nonuniform, incoherent background of a speckle image of an object, the method including the steps of:

illuminating an object with a source of at least partially coherent light so as to provide a reflected field of light;

sampling a first portion of the reflected field so as to provide a first speckle image therefrom;

sampling a second portion of the reflected field spatially separated from the first portion by at least a diameter of a speckle, so as to provide a second speckle image uncorrelated with the first;

subtracting the first and second speckle images so as to provide an output signal; and, rectifying the output signal, whereby the contribution of non-coherent light to the speckle image is removed.

14. A method as in claim 13, wherein the steps of sampling said first and second portions of the reflected field includes the further steps of:

providing an aperture disposed so as to sample the reflected field and provide a speckle image of said illuminated object;

disposing said aperture in a first position so as to provide a first speckle image; and moving said aperture to a second position disjointed from said first position by at least the diameter of a speckle, whereby said aperture provides a second speckle image uncorrelated with said first speckle image.

15. A method as in claim 13, wherein the step of sampling said first and second portions of the reflected field includes the further steps of:

disposing a first aperture so as to sample light reflected from the object and provide the first speckle image thereof; and disposing a second aperture in a position spatially separated from the position of said first aperture by at least the diameter of a speckle, so as to provide said uncorrelated second speckle image.

16. A method as in claim 13, including the further step of:

digitizing said first and second speckle images prior to the subtraction thereof.

17. A method as in claim 13, wherein said object has a surface texture characterized by features of given heights, said method further adapted to provide information regarding the surface texture and including the step of:

illuminating said object with coherent light having a coherence length less than the heights of said features.

* * * * *